United States Patent [19]
Ghosh

[11] Patent Number: 5,907,073
[45] Date of Patent: May 25, 1999

[54] AROMATIC ALKYLATION PROCESS

[75] Inventor: Ashim Kumar Ghosh, Houston, Tex.

[73] Assignee: Fina Technology, Inc., Dallas, Tex.

[21] Appl. No.: 09/030,285

[22] Filed: Feb. 24, 1998

[51] Int. Cl.⁶ .................................. C07C 2/68; B01J 29/06
[52] U.S. Cl. .............................................. 585/467; 502/67
[58] Field of Search ................................... 585/467, 446; 502/67

[56] References Cited

U.S. PATENT DOCUMENTS

| | | | |
|---|---|---|---|
| 3,308,069 | 3/1967 | Wadlinger et al. | 252/455 |
| 3,832,449 | 8/1974 | Rosinski et al. | 423/328 |
| 4,107,224 | 8/1978 | Dwyer | 260/671 R |
| 4,185,040 | 1/1980 | Ward et al. | 585/467 |
| 4,387,259 | 6/1983 | Barile | 585/467 |
| 4,642,226 | 2/1987 | Calvert et al. | 423/328 |
| 4,774,377 | 9/1988 | Barger et al. | 585/323 |
| 5,600,048 | 2/1997 | Cheng et al. | 585/449 |

FOREIGN PATENT DOCUMENTS

| | | |
|---|---|---|
| 0 159 846 | 10/1985 | European Pat. Off. . |
| 0 186 447 | 7/1986 | European Pat. Off. . |
| 0 467 007 | 1/1992 | European Pat. Off. . |

*Primary Examiner*—Glenn Caldarola
*Assistant Examiner*—Thuan D. Dang
*Attorney, Agent, or Firm*—Pamela S. Smith; William D. Jackson; M. Norwood Cheairs

[57] ABSTRACT

A process for the alkylation of an aromatic substrate over a molecular sieve zeolite catalyst involving supplying an aromatic substrate to a reaction zone containing the catalyst. The molecular sieve catalyst is an effective aromatic alkylation catalyst and comprises a modified zeolite beta alkylation catalyst having an intergrowth of a ZSM-12 crystalline framework within the crystalline framework of zeolite beta. An alkylating agent is also supplied to the reaction zone which is operated under temperature and pressure conditions effective to cause alkylation of the aromatic substrate by the alkylating agent. An alkylated substrate is recovered from the reaction zone.

22 Claims, 5 Drawing Sheets

AROMATIC ALKYLATION PROCESS

FIELD OF THE INVENTION

This invention involves an aromatic alkylation process involving alkylation of an aromatic substrate such as benzene over a modified zeolite beta aromatic alkylation catalyst incorporated a ZSM-12 crystalline structure.

BACKGROUND OF THE INVENTION

Aromatic conversion processes which are carried out over molecular sieve catalyst are well known in the chemical processing industry. Such aromatic conversion reactions include the alkylation of aromatic substrates such as benzene to produce alkyl aromatics such as ethylbenzene, ethyltoluene, cumene or higher aromatics and the transalkylation of polyalkyl benzenes to monoalkyl benzenes. Typically, an alkylation reactor which produces a mixture of mono- and poly- alkyl benzenes may be coupled through various separation stages to a downstream transalkylation reactor. Such alkylation and transalkylation conversion processes can be carried out in the liquid phase, in the vapor phase or under conditions in which both liquid and vapor phases are present.

An example of vapor phase alkylation is found in U.S. Pat. No. 4,107,224 to Dwyer. Here, vapor phase ethylation of benzene over a zeolite catalyst is accomplished in a down flow reactor having four series connected catalyst beds. The output from the reactor is passed to a separation system in which ethylbenzene product is recovered, with the recycle of polyethylbenzenes to the alkylation reactor where they undergo transalkylation reactions with benzene. The Dwyer catalysts are characterized in terms of those having a constraint index within the approximate range of 1–12 and include, with the constraint index in parenthesis, ZSM-5 (8.3), ZSM-11 (8.7), ZSM-12 (2), ZSM-35 (4.5), ZSM-38 (2), and similar materials.

U.S. Pat. No. 4,185,040 to Ward et al discloses an alkylation process employing a molecular sieve catalyst of low sodium content, less than 0.5 wt. % $Na_2O$, which is said to be especially useful in the production of ethylbenzene from benzene and ethylene and cumene from benzene and propylene. Examples of suitable zeolites include molecular sieves of the X, Y, L, B, ZSM-5, and omega crystal types, with steam stabilized hydrogen Y zeolite being preferred. Specifically disclosed is a steam stabilized ammonium Y zeolite containing about 0.2% $Na_2O$. Various catalyst shapes are disclosed in the Ward et al patent. While cylindrical extrudates may be employed, a particularly preferred catalyst shape is a so-called "trilobal" shape which is configured as something in the nature of a three leaf clover. The surface area/volume ratio of the extrudate should be within the range of 85–160 $in.^{-1}$. The alkylation process may be carried out with either upward or downward flow, the latter being preferred, and preferably under temperature and pressure conditions so that at least some liquid phase is present, at least until substantially all of the olefin alkylating agent is consumed. Ward et al states that rapid catalyst deactivation occurs under most alkylating conditions when no liquid phase is present.

U.S. Pat. No. 4,774,377 to Barger et al discloses an alkylation/transalkylation process which involves the use of separate alkylation and transalkylation reaction zones, with recycle of the transalkylated product to an intermediate separation zone. In the Barger process, the temperature and pressure conditions are adjusted so that the alkylation and transalkylation reactions take place in essentially the liquid phase. The transalkylation catalyst is an aluminosilicate molecular sieve including X-type, Y-type, ultrastable-Y, L-type, omega type and mordenite type zeolites with the latter being preferred. The catalyst employed in the alkylation reaction zone is a solid phosphoric acid containing material. Aluminosilicate alkylation catalysts may also be employed and water varying from 0.01 to 6 volume percent is supplied to the alkylation reaction zone. The output from the alkylation reaction zone is supplied to first and second separation zones. Water is recovered in the first separation zone. In the second separation zone, intermediate aromatic products and trialkyl aromatic and heavier products are separated to provide an input to the transalkylation reaction zone having only dialkyl aromatic components, or diethylbenzene in the case of an ethylbenzene manufacturing procedure or diisopropylbenzene in the case of cumene production. A benzene substrate is also supplied to the transalkylation zone for the transalkylation reaction and the output from the transalkylation zone is recycled to the first separation zone. The alkylation and transalkylation zones may be operated in downflow, upflow, or horizontal flow configurations.

Another alkylation procedure is disclosed in European Patent Application No. 272,830 to Ratcliffe et al. The Ratcliffe procedure employs molecular sieve alkylation catalysts which have been treated in a manner to improve selectivity to monoalkylation, specifically in the propylation of benzene to produce cumene. Selectivity is said to be increased by at least one percentage point by first depositing a carbonaceous material on the catalyst and then subjecting the resultant carbon containing catalyst particles to combustion. Specific zeolitic crystalline molecular sieves include those selected from the group of Y zeolites, fluorided Y zeolites, X zeolites, zeolite beta, zeolite L, and zeolite omega. The zeolites may be modified to arrive at products of reduced alumina content and reduced sodium content.

EPA publication 467,007 to Butler discloses other processes having separate alkylation and transalkylation zones employing various molecular sieve catalysts and with the output from the transalkylation reactor being recycled to an intermediate separation zone. Here, a benzene separation zone, from which an ethylbenzene/polyethylbenzene fraction is recovered from the bottom with recycling of the overhead benzene fraction to the alkylation reactor is preceded by a prefractionation zone. The prefractionation zone produces an overhead benzene fraction which is recycled along with the overheads from the benzene column and a bottom fraction which comprises benzene, ethylbenzene and polyethylbenzene. Two subsequent separation zones are interposed between the benzene separation zone and the transalkylation reactor to provide for recovery of ethylbenzene as the process product and a heavier residue fraction. The polyethylbenzene fraction from the last separation zone is applied to the transalkylation reactor and the output there is applied directly to the second benzene separation column or indirectly through a separator and then to the second benzene separation column. Butler discloses that the alkylation reactor may be operated in the liquid phase with a catalyst such as zeolite-beta, zeolite-Y or zeolite-omega or in the vapor phase employing a catalyst such as silicalite or ZSM-5.

SUMMARY OF THE INVENTION

In accordance with the present invention there is provided a process for the alkylation of aromatic substrate over a molecular sieve zeolite catalyst. In carrying out the invention, a feedstock containing an aromatic substrate is supplied to a reaction zone containing a shape-selective molecular sieve catalyst which is an effective aromatic alkylation catalyst. The molecular sieve catalyst comprises a modified zeolite beta alkylation catalyst having an intergrowth of a ZSM-12 crystalline framework with the crystalline framework of zeolite beta. An alkylating agent is also supplied to the reaction zone which is operated under temperature and pressure conditions effective to cause alkylation of the aromatic substrate by the alkylating agent. An alkylated substrate is recovered from the reaction zone.

In a preferred embodiment of the invention, the zeolite molecular sieve catalyst is characterized by the process of claim 1 wherein said molecular sieve catalyst is characterized by an x-ray diffraction pattern characteristic of zeolite beta and having a maximum peak at an interplanar spacing D of 4.0/±0.1A and secondary peaks $S_1$ at a D spacing of 11.4±0.2A, $S_2$ at a D spacing of 4.2±0.1A and a secondary doublet $S_3$, $S_4$ at D spacings within the range of about 3.0–3.4±0.1A, and further comprising a first secondary peak characteristic of ZSM-12 occurring at an interplanar spacing D 10.0±2A and additional secondary peaks characteristic of ZSM-12 at D spacings less than the D spacing of said primary peak but greater than the D spacing of said doublet $S_3$, $S_4$. Preferably, the aromatic substrate is benzene and the alkylating agent is a $C_2$–$C_4$ alkylating agent. Preferably, the alkylating agent is an ethylating agent, specifically ethylene.

In a specific embodiment of the invention, there is provided a process for the production of ethylbenzene by the liquid phase ethylation of benzene. In this embodiment of the invention, benzene and an ethylating agent are supplied to a reaction zone comprising a modified zeolite beta alkylation catalyst having an intergrowth ZSM-12 crystalline framework within the crystalline framework of zeolite beta. The reaction zone is operated under temperature and pressure conditions to maintain the benzene in the liquid phase to cause monoethylation of the benzene under conditions which the xylene produced in the reaction zone is no more than 0.05 wt. % based upon the amount of ethylbenzene produced. In one embodiment of the invention, the molecular sieve catalyst is in the hydrogen form; in another, it is in an exchanged form which incorporates lanthanum ions in the crystalline structure of the molecular sieve. Preferably, a plurality of series-connected reaction stages are employed. It is also preferred that the toluene in the reaction zone is no more than 0.1 wt. % based upon the amount of ethylbenzene produced.

DETAILED DESCRIPTION OF THE INVENTION

The present invention involves alkylation of an aromatic substrate in a reaction zone containing a modified zeolite beta alkylation catalyst which preferably is carried out under relatively mild liquid phase alkylation conditions. The invention is especially applicable to the ethylation of benzene under mild liquid phase conditions producing little or no xylenes and the invention will be described specifically by reference to the production of ethylbenzene. However, other alkylation reactions may be utilized in carrying out the invention. For example, the invention may be applied to the reaction of propylene with benzene to produce cumene. Also, while olefinic alkylating agents normally will be employed, other alkylating agents such as alkynes, alkyl halides, alcohols, ethers, and esters as disclosed, for example in U.S. Pat. No. 3,551,510 to Pollitzer et al. may be used. Also other aromatic substrates such as toluene and xylene may be subject to alkylation in accordance with the invention.

The alkylation catalyst employed in the present invention is zeolite beta which has been modified as indicated by its X-ray diffraction pattern to incorporate a ZSM-12 crystalline framework with the crystalline framework of the zeolite beta. Zeolite beta and zeolite ZSM-12 are in themselves well-known molecular sieve catalysts and basic procedures for the preparation of these zeolites are well known to those skilled in the art and are exemplified by the procedures for preparation of crystalline zeolite beta as disclosed in U.S. Pat. Nos. 3,308,069 (Wadlinger et al.) and 4,642,226 (Calvert et al.) and European Patent Application Nos. 159, 856 (Reuben); 165,208 (Bruce et al.); 186,447 (Kennedy et al.), the entire disclosures of which are incorporated herein by reference. The zeolite beta can be prepared to have a low sodium content, i.e. less than 0.2 wt. % expressed as $Na_2O$ and the sodium content can be further reduced to a value of about 0.02 wt. % by the ion exchange treatment described below and which is preferred.

As disclosed in the above-referenced U.S. patents to Wadlinger et al., and Calvert et al, zeolite beta can be produced by the hydrothermal digestion of a reaction mixture comprising silica, alumina, sodium or other alkyl metal oxide, and an organic templating agent. Typical digestion conditions include temperatures ranging from slightly below the boiling point of water at atmospheric pressure to about 170° C. at pressures equal to or greater than the vapor pressure of water at the temperature involved. The reaction mixture is subjected to mild agitation for periods ranging from about one day to several months to achieve the desired degree of crystallization to form the zeolite beta. The resulting zeolite beta is normally characterized by a silica to alumina molar ratio (expressed as $SiO_2/Al_2O_3$) of between about 20 and 50.

The zeolite beta is then subjected to ion-exchange with ammonium ions at uncontrolled pH. It is preferred that an aqueous solution of an inorganic ammonium salt, e.g., ammonium nitrate, be employed as the ion-exchange medium. Following the ammonium ion-exchange treatment, the zeolite beta is filtered, washed and dried, and then calcined at a temperature between about 530° C. and 580° C. for a period of two or more hours. The calcined zeolite can, if desired, be dealuminated by steaming in order to further enhance the silica to alumina ratio. For example, steaming can take place at a temperature between about 550° C. and 750° C. for approximately two hours. The dealuminated zeolite can then be subjected to one or more successive ammonium ion-exchanges under acid conditions resulting in proton ion exchange. The ion exchanged zeolite beta normally will have a silica to alumina male ratio between about 50 and 350 usually between about 70 and 200.

After the final ammonium ion-exchange, the zeolite beta is mixed with a binder, such as alumina sol, gamma-alumina or other refractory oxides to produce a mulled zeolite-binder mixture containing about 20% binder. Normally alumina binder is employed. This mixture is then pelletized by any suitable technique, such as extrusion, and the resulting pellets dried. The pelletized binder-beta zeolite product is then calcined under conditions sufficient to place the zeolite in its active hydrogen form. Calcination at a temperature of approximately 530° C. for two to four hours is normally used.

Similar protocols can be followed in the preparation of ZSM-12. Zeolite ZSM-12 and its preparation is disclosed in U.S. Pat. No. 3,832,449 to Rosinski et al., the entire disclosure of which is incorporated by reference. As disclosed in Rosinski, ZSM-12 can be prepared by the hydrothermal digestion of reaction mixture of colloidal silica sol, a source of alumina such as sodium aluminate and a triethylamine or tetraethylammonium organic templating agent. The digestion conditions may be similar to those described above, e.g. about 175° C. for a one-two week period followed by high temperature calcination. Similarly, as described above, the zeolite beta can be formed with a refractory oxide binder and pelletized.

Zeolite beta and zeolite ZSM-12 can be characterized by case by their crystal structure symmetry and most objectively by their X-ray diffraction patterns. Both zeolite beta and zeolite ZSM-12 are molecular sieves of medium pore sizes, about 5–8 angstroms, and contain 12 ring channel systems. Zeolite beta is of tetragonal symmetry $P4_122$, a=12.7, c=26.4 Å(W. M. Meier and D. H. Olson Butterworth, *Atlas of Zeolite Structure Types*, Heinemann, 1992, p. 58); ZSM-12 is generally characterized by monoclinic symmetry. The pores of zeolite beta are generally circular along the 001 plane with a diameter of about 5.5 angstroms and are elliptical along the 100 plane with diameters of about 6.5 and 7.6 angstroms. ZSM-12 likewise has pore channels of an elliptical configuration having a diameter in the main direction of 5.7×6.1 angstroms.

As noted above, the X-ray diffraction patterns provide an objective system for characterizing the zeolite beta and ZSM-12. Zeolite beta is generally characterized by a very strong primary peak of maximum intensity at an interplanar spacing, D, of about 4 angstroms (A). Secondary peaks appear at about 11.3 A +/−0.1 A and at about 4.2 A +/−0.1 with a doublet occurring at D-spacings in the range of about 3.0 to 3.3.

Figure 1:
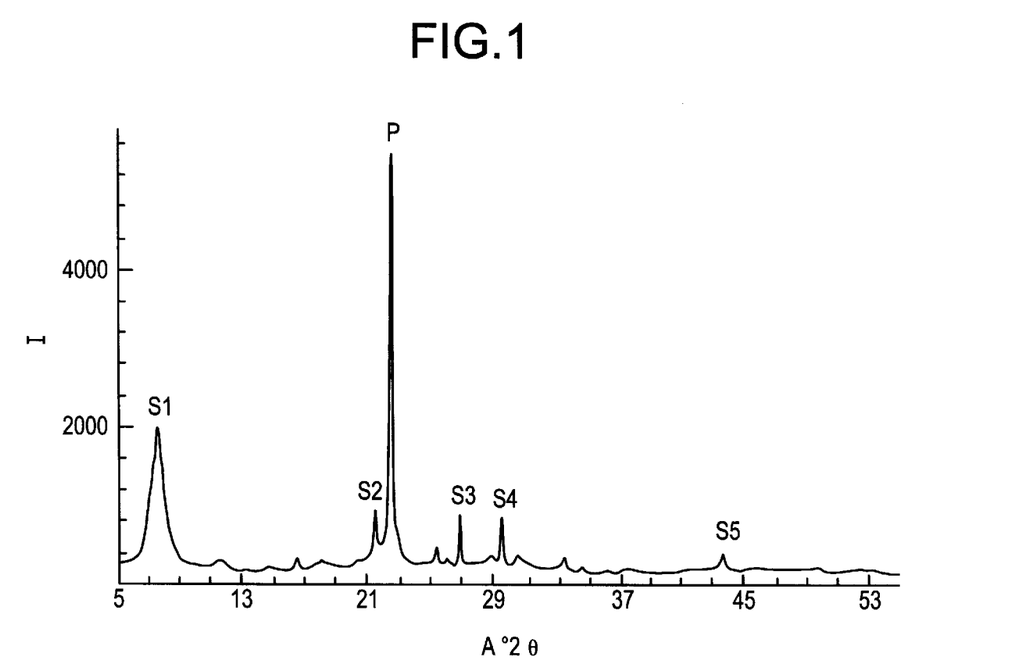
FIG. 1 is an x-ray diffraction pattern of zeolite beta.

An X-ray diffraction pattern for a zeolite beta as found in Perez-Pariente, J., et al, *Applied Catalysis*, 31, 35 (1987) is shown in FIG. 1 in which the intensity I as measured by the count rate is plotted in the ordinate versus the interplanar spacing as indicated by the refraction angle A as 2θ measured from the Bragg equation on the abscissa. In FIG. 1, the maximum intensity signal P, occurring at about 22.4° 2θ corresponds to a D-spacing of about 4 angstroms. The secondary peaks designated in FIG. 1 by the designations S1–S5 indicate interplanar D-spacings of about 11.3 A for S1, about 4.2 A for S2, about 3.0–3.3A for the doublet S3, S4, and about 2.1A for the minor peak S5 appearing at about 43.6° 2θ.

As described in the aforementioned patent to Rosinski, ZSM-12 can be characterized by an X-ray diffraction pattern summarized in Rosinski as having very strong (VS), medium (M) and weak (W) peaks as follows:

TABLE 1

| INTERPLANAR SPACING D (A) | RELATIVE INTENSITY |
| --- | --- |
| 11.9 ± 0.2 | M |
| 10.1 ± 0.2 | M |
| 4.76 ± 0.1 | W |
| 4.29 ± 0.08 | VS |
| 3.98 ± 0.08 | M |
| 3.87 ± 0.07 | VS |
| 3.49 ± 0.07 | W |
| 3.38 ± 0.07 | M |
| 3.20 ± 0.06 | W |
| 3.05 ± 0.05 | W |
| 2.54 ± 0.03 | W |

The modified zeolite employed in the present invention can be distinguished in terms of its X-ray diffraction pattern from the X-ray diffraction patterns of zeolite beta and zeolite ZSM-12 in several important respects, as described below and as indicated by experimental work carried out the respecting current invention. In the experimental work, two forms of modified zeolite beta were employed, one a hydrogen form of zeolite beta and the other a lanthanum exchanged form of modified zeolite beta. In each case, a commercially available form of zeolite beta powder commercially available from CU Chemie Uetikon AG (Switzerland) was used as the starting material. This commercially-available material, designated as Uetikon PB-2, had a somewhat higher silica/alumina ratio (about 40) than the values of about 15 to 25 commonly associated with commercial zeolite beta available from the same source. In experimental work regarding this zeolite beta powder, it was found to have a somewhat lower surface area, about 568 m$^2$/g as compared with a conventional zeolite beta from the same manufacturer (758 m$^2$/g) and another zeolite beta available from another source (about 750 m$^2$/g). As indicated by the X-ray diffraction analysis discussed below, this reduced surface area was found to be due to the intergrowth of a second zeolite, identified as zeolite ZSM-12, during the synthesis procedure. The modified zeolite beta employed in the experimental work relating to the present invention was noted, previously used in the hydrogen form and in the lanthanum exchange form.

An analysis of several modified zeolite betas as thus prepared together with conventional zeolite betas are shown in the following table:

TABLE 2

| Sample | Elemental Analysis, wt %[1] | | | | | Particle Size μm | Surface Area m2/g |
| --- | --- | --- | --- | --- | --- | --- | --- |
| | SiO2 | Al2O3 | Na2O | K2O | SAR | | |
| 1 | 93.6 | 6.3 | 0.1 | | 25 | 0.1–0.7 | 750 |
| 2 | 95.54 | 4.13 | 0.16 | 0.17 | 39.24 | 0.3–0.8 | 576 |
| 3 | 93.88 | 3.67 | 0.02 | 0.06 | 43.44 | | 568 |
| 4 | | | | | | | 471 |
| 5 | 95.40 | 3.64 | 0.02 | 0.03 | 44.50 | | |
| 6 | | | | | | | 459 |

In the foregoing table, the elemental analysis presented is expressed in weight percent on an anhydrous basis. Sample 1 is a commercially-available zeolite beta of a moderately low silica alumina ratio of 25. Sample 2 is the zeolite beta powder identified above as Uetikon PB-2 in an as received basis, that is without ion exchanging. Sample 3 represents the ammonium-exchanged-style zeolite beta powder prior to extrusion with the binder and calcination, and Sample 4 represents the corresponding catalyst after calcination and extrusion with the alumina binder to provide 20% alumina binder. Sample 5 represents the lanthanum exchange zeolite beta powder and Sample 6 represents the catalyst prepared from the lanthanum exchanged beta powder, again extruded with 20% alumina and calcined at 530° C.

The starting batches of the commercially acquired zeolite beta identified as PB-2 was subjected to repeated ammonium ion exchange procedures as described below.

Repeated ammonium ion exchange treatments were done by submersing the zeolite powder (Sample 2 in Table 2) in an aqueous solution of ammonium nitrate having a normality of about 2 at a zeolite to ammonium nitrate ratio of about 1:1. The zeolite beta was submersed in the ion exchange medium under mild agitation at 85–95° C. for a period of more than 4 hours. pH of the exchange medium was not controlled but measured at 1.5 to 4.0. The zeolite beta was then filtered, washed with deionized water and dried at 100° C. for at least two hours. This sample was referred as $NH_4$-Beta (Sample 3) in Table 2. The ammonium exchanged zeolite was further ion exchanged with $La^{3+}$ ions by submersing the zeolite powder in an aqueous solution under mild agitation at 85–95° C. (for 5 hours) and then adding aqueous solution containing lanthanum nitrate. Nominal loading of $La^{3+}$ was 0.5 wt %. The zeolite was then filtered, washed with deionized water and dried at 110° C. for at least two hours. This sample was referred as $LaNH_4$-Beta (Sample 5) in Table 2.

The powder $NH_4$-Beta (Sample 3) and $LaNH_4$-Beta (Sample 5) were mulled with nitric acid treated alumina and extruded into 1/16-inch pellets. The resulting extruded zeolite pellets were then calcined in an oven under air in a programmed temperature to a maximum of 530° C. The $NH_4$-Beta and $LaNH_4$-Beta were thus converted into H-Beta catalyst and LaH-Beta catalyst, respectively, as the $NH_3$ was evolved during calcination of the extrudates at 530° C.

Figure 2:
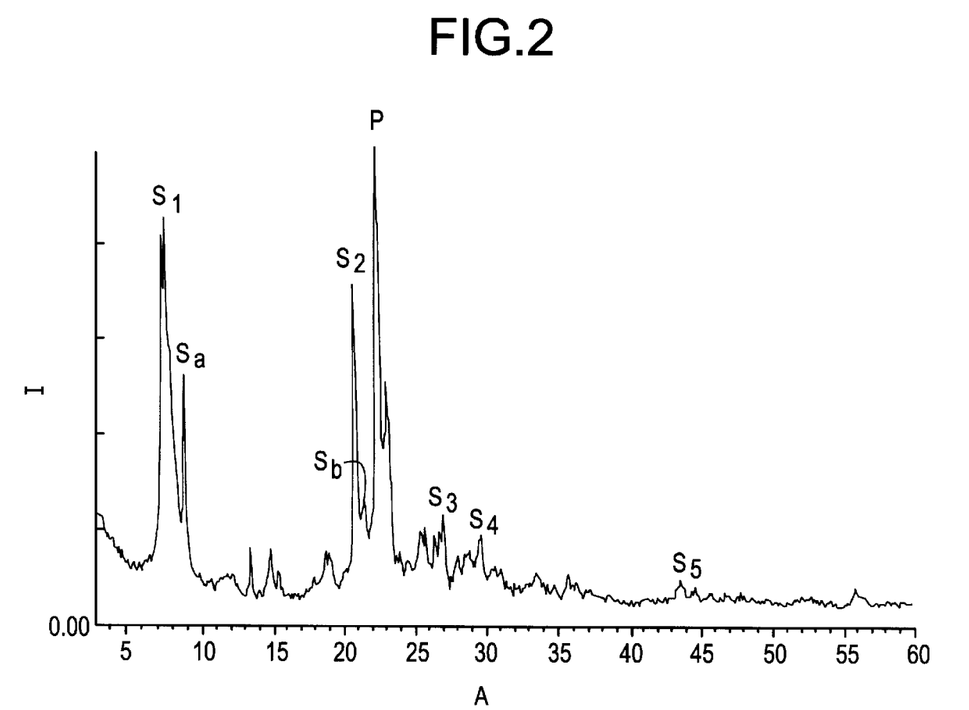
FIG. 2 is an x-ray diffraction pattern of a modified form of zeolite beta incorporating a ZSM-12 crystalline framework intergrowth.
Figure 3:
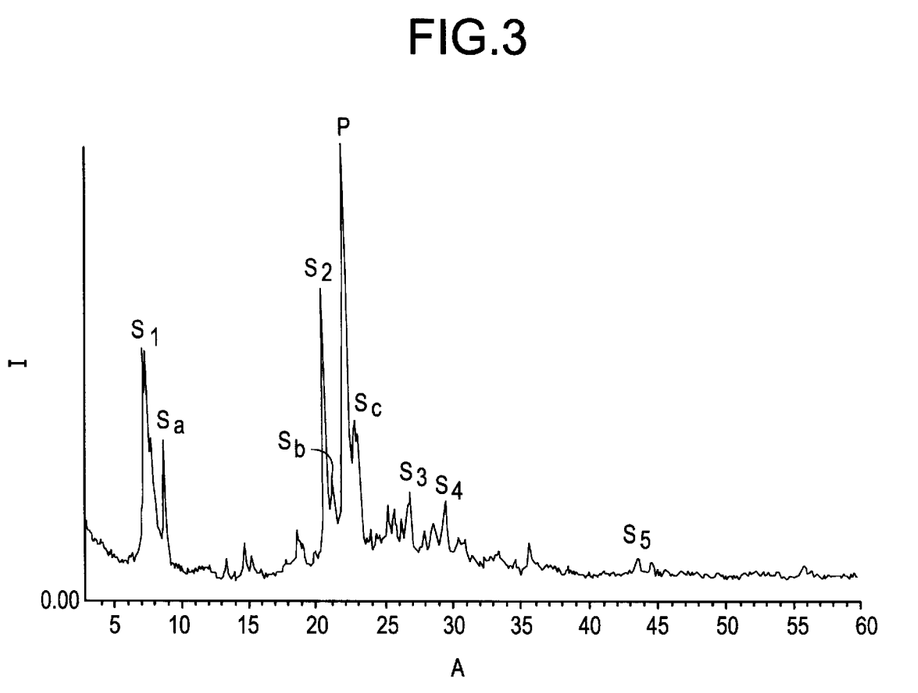
FIG. 3 is an x-ray diffraction pattern of modified zeolite beta after ammonium ion exchange.

X-ray diffraction patterns for the powder zeolite samples, identified above as PB-2 before and after ammonium ion exchange, are shown in FIGS. 2 and 3, respectively. In each of FIGS. 2 and 3 the count rate I is plotted on the ordinate versus the Bragg angle 2θ A in degrees plotted on the abscissa. Thus, as can be seen by a comparison of FIGS. 2 and 3, the X-ray diffraction patterns are similar but with the peaks designated in FIG. 3 as $S_1$, $S_a$, and $S_c$ being of somewhat lower intensity than the corresponding peaks appearing in the X-ray diffraction pattern of the as received materials shown in FIG. 2.

The tabular data corresponding to the X-ray diffraction patterns for the various zeolite beta patterns shown in FIGS. 1, 2 and 3 are reproduced in Table 3 below.

TABLE 3

| β Powder | | Uetikon PB-2 | | | $NH^+β$ Powder | | |
|---|---|---|---|---|---|---|---|
| d-spacing (nm) | Rel. Intensity (%) | d-spacing (nm) | 2θ | Rel. Intensity (%) | d-spacing (nm) | 2θ | Rel. Intensity (%) |
| 1.13 | 39 | 1.151 | 7.68 | 85.33 | 1.159 | 7.62 | 54.85 |
|  |  |  |  |  | 1.107 | 7.98 | 35.63 |
|  |  | >0.999 | 8.84 | 52.31 | 0.996 | 8.87 | 35.20 |
| 0.76 | 3 |  |  |  |  |  |  |
|  |  | 0.725 | 12.20 | 10.67 | 0.725 | 12.21 | 7.51 |
| 0.67 | 2 | 0.656 | 13.48 | 16.02 | 0.658 | 13.46 | 8.71 |
|  |  | 0.598 | 14.81 | 15.61 | 0.598 | 14.81 | 12.38 |
|  |  | 0.576 | 15.36 | 11.16 | 0.580 | 15.27 | 9.52 |
|  |  | 0.495 | 17.89 | 9.81 | 0.498 | 17.80 | 8.57 |
|  |  | 0.472 | 18.80 | 15.24 | 0.471 | 18.81 | 14.85 |
|  |  | 0.466 | 19.01 | 14.63 | 0.441 | 20.10 | 10.19 |
| 0.42 | 15 | 0.425 | 20.89 | 71.11 | 0.424 | 20.92 | 67.90 |
|  |  | 0.41 | 21.49 | 25.8 | 0.414 | 21.43 | 25.75 |
| 0.40 | 100 | 0.394 | 22.55 | 100 | 0.395 | 22.47 | 100 |
|  |  | 0.38 | 23.14 | 50.6 | 0.383 | 23.22 | 35.80 |
|  |  | 0.373 | 23.82 | 13.98 | 0.371 | 23.94 | 14.71 |
|  |  | 0.363 | 24.50 | 13.20 | 0.362 | 24.58 | 12.95 |
|  |  | 0.349 | 25.46 | 19.25 | 0.351 | 25.36 | 20.00 |
|  |  | 0.346 | 25.74 | 20.02 | 0.345 | 25.80 | 19.44 |
|  |  | 0.337 | 26.43 | 18.23 | 0.337 | 26.40 | 17.18 |
|  |  | 0.332 | 26.82 | 19.33 |  |  |  |
|  |  | 0.329 | 27.10 | 22.64 | 0.329 | 27.04 | 23.00 |
|  |  | 0.318 | 28.05 | 14.10 | 0.318 | 28.03 | 14.39 |
|  |  | 0.312 | 28.60 | 14.67 | 0.311 | 28.73 | 16.12 |
|  |  | 0.310 | 28.82 | 15.53 |  |  |  |
| 0.30 | 12 | 0.301 | 29.64 | 18.55 | 0.302 | 29.59 | 20.85 |
|  |  | 0.292 | 30.59 | 11.77 | 0.293 | 30.51 | 12.80 |
|  |  | 0.288 | 31.04 | 11.48 | 0.288 | 31.00 | 12.45 |
|  |  | 0.267 | 33.49 | 10.75 | 0.268 | 33.40 | 9.49 |
|  |  | 0.258 | 34.70 | 8.26 | 34.67 | 0.258 | 7.90 |
|  |  | 0.251 | 35.72 | 10.30 | 0.251 | 35.71 | 11.29 |
|  |  | 0.248 | 36.24 | 8.87 | 0.234 | 38.52 | 6.35 |
| 0.21 | 6 | 0.207 | 43.62 | 9.48 | 0.208 | 43.58 | 8.50 |
|  |  | 0.203 | 44.62 | 7.97 | 0.203 | 44.68 | 7.69 |
|  |  | 0.165 | 55.84 | 7.56 | 0.165 | 55.84 | 6.56 |

As can be shown by the X-ray diffraction patterns in FIGS. 1, 2 and 3 and Table 2, the modified zeolite beta employed in the present invention has characteristics both of zeolite beta and zeolite ZSM-12. Referring to FIG. 3, the modified zeolite beta has the peaks characteristic of conventional zeolite beta. Those include maximum or primary peak P appearing at an interplanar spacing of about 4.0 +/−0.1A and secondary peaks $S_1$ and $S_2$ appearing at 11.4±0.2A and 4.2±0.1A, respectively. The peak $S_2$ for the modified beta is of substantially greater intensity than the corresponding peak S-2 shown in FIG. 1. In addition, a characteristic doublet $S_3$, $S_3$ appears at D-spacings of about 3.0–3.4±0.1A, and a peak $S_5$ corresponds to the zeolite beta peak S-5. In addition to the peaks characteristic of zeolite beta, the modified beta of the present invention shows additional secondary peak characteristics which are characteristic of ZSM-12. This includes a pronounced secondary peak Sa occurring at an interplanar D-spacing of about 10.0A and additional secondary peaks Sb and Sc at D-spacing of about 4.1A and 3.8A. Further relatively minor peaks are found at D-spacings which are less than the spacing of the primary zeolite beta peak at a D-spacing of about 4A but more than the D-spacings observed for the characteristic doublet $S_3$, $S_4$.

In experimental work respecting the present invention, both the hydrogen modified zeolite beta and the lanthanum exchange modified zeolite beta were used in liquid phase alkylation of an aromatic substrate, benzene, employing ethylene as the alkylating agent. The reactor used in the experimental work was a 22 milliliter vertical reactor which was packed with 10 liters of catalyst particles ranging in size from 10–20 mesh, and the void space was filled with silicon carbide inert material. The reactor was equipped with four thermocouples designated TC #2–TC #5 spaced from the top of the bed for TC #2 to the bottom of the bed for TC #5. The reactor was operated in an upflow mode with benzene and ethylene supplied to the bottom inlet to the reactor. The reactor was operated under liquid phase conditions at an inlet temperature of 200° C. and an inlet pressure of 600 psig. The benzene was injected at a liquid hourly space velocity of 30 hours$^{-1}$, and the ethylene was injected to provide a benzene/ethylene mole ratio of 12:1.

Figure 4:
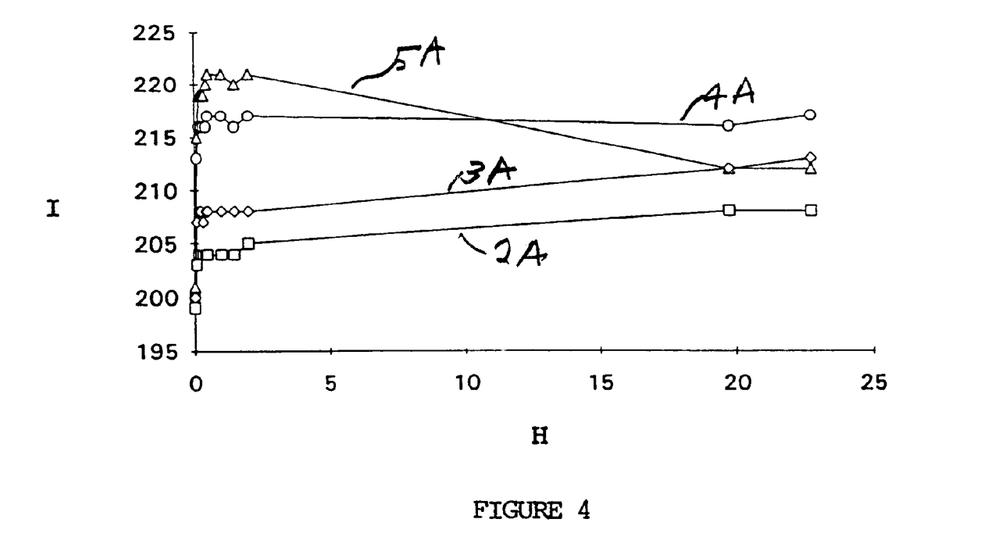
FIG. 4 is a graph illustrating temperature profiles for an alkylation reaction carried out over modified zeolite beta in the hydrogen form.
Figure 5:
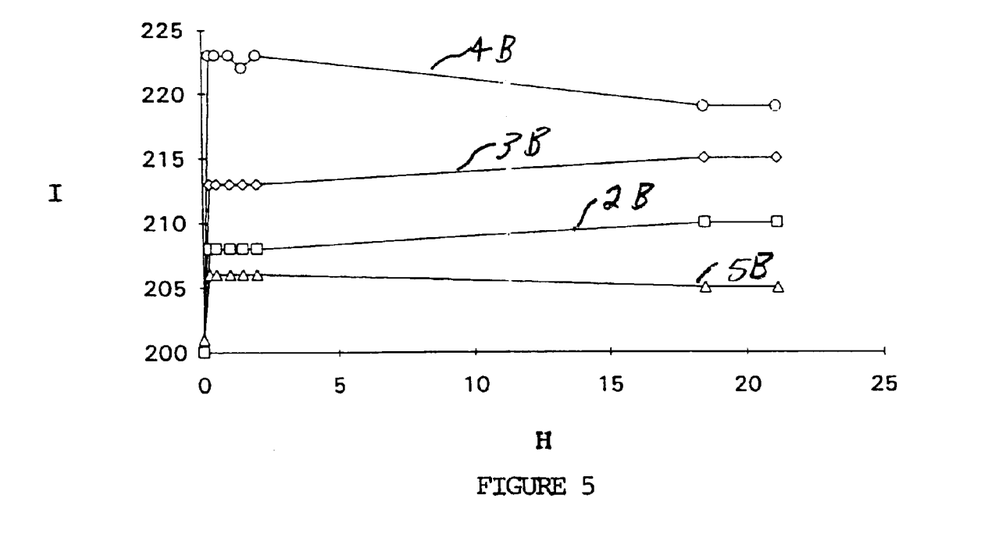
FIG. 5 is a graph illustrating temperature profiles of an alkylation reaction carried out over modified zeolite beta in the lanthanum exchange form.

FIGS. 4 and 5 show temperature profiles versus the age of the catalyst in hours for the modified zeolite beta in the hydrogen form in FIG. 4 and the modified zeolite beta in the lanthanum form in FIG. 5. In FIG. 4, curves 2A, 3A, 4A, and 5A are graphs of the temperature T in degrees C on the ordinate versus catalyst age H in hours on the abscissa, as observed at thermocouples TC #2, TC #3, TC #4, and TC #5, respectively. FIG. 5 is a similar graph showing temperature I in degrees C on the ordinate versus the catalyst age H in hours on the abscissa plotted as curves 2B, 3B, 4B, and 5B for the thermocouples TC #2, TC #3, TC #4, and TC #5, respectively.

As can be seen from an examination of FIGS. 4 and 5, the fresh catalyst in the hydrogen form showed progressively decreasing temperature through the catalyst bed until near the end of the test where it showed an initial exotherm in the lower portion of the catalyst bed with the temperature then declining. The modified zeolite beta in the lanthanum form showed uniformly an initial increase in temperature from the bottom thermocouple to the next thermocouple followed by a progressively decreasing temperature throughout the remainder of the catalyst bed. This profile was relatively constant with age.

The product distribution of the alkylation products produced using the hydrogen form of the modified zeolite beta and the lanthanum form of the modified zeolite beta are shown in Tables 4 and 5 for the hydrogen form of the catalyst and in Tables 6 and 7 for the lanthanum exchange form of the catalyst. Each column indicates the parameter stated for a given age of the run which progressively increases from the left to the right for each table. In the tables, the abbreviations EB and DEB are used for ethylbenzene and diethylbenzene, respectively.

TABLE 4

| Catage/Hour | 0.25 | 0.5 | 1.0 | 1.5 | 2.0 | 19.75 |
|---|---|---|---|---|---|---|
| EB, wt % | 10.09 | 10.15 | 9.46 | 9.50 | 10.22 | 10.06 |
| Yield rel to EB | | | | | | |
| Toluene, PPM | 704 | 699 | 751 | 747 | 704 | 696 |
| Xylenes, PPM | 0 | 0 | 0 | 0 | 0 | 0 |
| Cumene, PPM | 0 | 0 | 0 | 0 | 0 | 0 |
| Ethyltoluene, PPM | 0 | 0 | 0 | 0 | 0 | 0 |
| Butylbenzene, PPM | 862 | 867 | 1173 | 968 | 831 | 795 |
| DEB, wt % | 6.47 | 6.56 | 5.75 | 6.19 | 6.26 | 6.20 |
| Heavies, wt % | 0.32 | 0.37 | 0.45 | 0.54 | 0.39 | 0.36 |
| % Mole Selectivity | | | | | | |
| Xylenes | 0 | 0 | 0 | 0 | 0 | 0 |
| EB | 93.56 | 93.41 | 94.12 | 93.46 | 93.89 | 93.96 |
| DEB | 4.79 | 4.87 | 4.28 | 4.58 | 4.65 | 4.61 |
| EB + DEB | 98.35 | 98.28 | 98.40 | 98.04 | 98.53 | 98.57 |

TABLE 5

| Catage/Hour | 0.25 | 0.5 | 1.0 | 1.5 | 2.0 |
|---|---|---|---|---|---|
| EB, wt % | 9.58 | 9.63 | 9.76 | 9.88 | 9.69 |
| Yield rel to EB | | | | | |
| Toluene, PPM | 731 | 727 | 717 | 719 | 722 |
| Xylenes, PPM | 0 | 0 | 0 | 0 | 0 |
| Cumene, PPM | 0 | 0 | 0 | 0 | 0 |
| Ethyltoluene, PPM | 0 | 0 | 0 | 0 | 0 |
| Butylbenzene, PPM | 1274 | 1008 | 737 | 689 | 660 |
| DEB, wt % | 5.72 | 5.72 | 5.81 | 5.85 | 5.79 |
| Heavies, wt % | 0.49 | 0.51 | 0.48 | 0.44 | 0.41 |
| % Mole Selectivity | | | | | |
| Xylenes | 0 | 0 | 0 | 0 | 0 |
| EB | 94.05 | 94.09 | 94.03 | 94.10 | 94.12 |
| DEB | 4.26 | 4.26 | 4.32 | 4.36 | 4.31 |
| EB + DEB | 98.31 | 98.35 | 98.35 | 98.45 | 98.44 |

TABLE 6

| Catage/Hour | 0.25 | 0.5 | 1.0 | 1.5 | 2.0 | 18.83 | 21.25 | 43 | 46.08 |
|---|---|---|---|---|---|---|---|---|---|
| EB, wt % | 9.27 | 9.62 | 9.62 | 9.58 | 9.60 | 9.55 | 9.60 | 9.16 | 9.42 |
| Yield rel to EB | | | | | | | | | |
| Toluene, PPM | 755 | 717 | 728 | 700 | 718 | 722 | 708 | 796 | 786 |
| Xylenes, PPM | 0 | 0 | 0 | 0 | 0 | 0 | 0 | 0 | 0 |
| Cumene, PPM | 0 | 0 | 0 | 0 | 0 | 0 | 0 | 0 | |
| Ethyltoluene, PPM | 0 | 0 | 0 | 0 | 0 | 0 | 0 | 0 | 0 |
| Butylbenzene, PPM | 1802 | 1434 | 1216 | 1096 | 1030 | 837 | 844 | 917 | 934 |
| DEB, wt % | 5.80 | 6.04 | 6.04 | 6.03 | 0.06 | 6.23 | 6.28 | 6.22 | 6.48 |
| Heavies, wt % | 0.26 | 0.27 | 0.27 | 0.27 | 0.28 | 0.29 | 0.29 | 0.38 | 0.38 |

TABLE 6-continued

| % Mole Selectivity | | | | | | | |
|---|---|---|---|---|---|---|---|
| Xylenes | 0 | 0 | 0 | 0 | 0 | 0 | 0 |
| EB | 94.09 | 94.01 | 94.02 | 94.06 | 94.01 | 93.79 | 93.68 |
| DEB | 4.31 | 4.49 | 4.49 | 4.48 | 4.50 | 4.63 | 4.65 |
| EEB + DEB | 98.40 | 98.50 | 98.51 | 98.54 | 98.51 | 98.41 | 98.34 |

TABLE 7

| Catage/Hour | 0.25 | 0.5 | 1.0 | 1.5 | 2.0 | 18.5 | 21.16 |
|---|---|---|---|---|---|---|---|
| EB, wt % | 9.47 | 9.63 | 9.65 | 9.69 | 9.54 | 9.79 | 9.64 |
| Yield rel to EB | | | | | | | |
| Toluene, PPM | 728 | 717 | 725 | 712 | 712 | 705 | 708 |
| Xylenes, PPM | 0 | 0 | 0 | 0 | 0 | 0 | 0 |
| Cumene, PPM | 285 | 280 | 249 | 248 | 241 | 225 | 0 |
| Ethyltoluene, PPM | 0 | 0 | 0 | 0 | 0 | 0 | 0 |
| Butylbenzene, PPM | 1309 | 1163 | 1067 | 1001 | 1016 | 899 | 861 |
| DEB, wt % | 6.22 | 6.30 | 6.33 | 6.33 | 6.58 | 6.46 | 6.31 |
| Heavies, wt % | 0.29 | 0.30 | 0.30 | 0.31 | 0.34 | 0.32 | 0.32 |
| % Mole Selectivity | | | | | | | |
| Xylenes | 0 | 0 | 0 | 0 | 0 | 0 | 0 |
| EB | 93.80 | 93.77 | 93.79 | 93.81 | 92.76 | 93.69 | 93.74 |
| DEB | 4.62 | 4.67 | 4.69 | 4.70 | 4.82 | 4.78 | 4.68 |
| EB + DEB | 98.42 | 98.97 | 98.97 | 98.51 | 98.96 | 98.95 | 98.96 |

As shown in the tables, the modified form of the zeolite beta catalyst produces a very low xylene content (actually zero in every case) and also a lower than expected toluene content.

Similarly, the hydrogen form of the modified zeolite beta consistently showed no cumene or ethyltoluene production with heavies content based upon ethylbenzene production of less than 0.5 wt. %. The mole selectivity to ethylbenzene was high—more than 90% in every case—and the diethylbenzene content was maintained relatively low at a value less than 5 wt. %. The lanthanum exchanged modified zeolite beta generally showed similar results although some cumene production was observed, as shown in Table 7. The lanthanum exchanged modified beta showed a slightly lower heavies make than the hydrogen form. This was accompanied by a slight increase in the butylbenzene concentration in the effluent.

Table 8 illustrates the results of experimental work carried out over the hydrogen form of the modified zeolite beta with different benzene/ethylene mole ratios. As shown by the data presented in Table 8, an increase in the ethylene injection rate (as indicated by a decrease in the benzene/ethylene mole ratio) resulted in a modest increase in ethylbenzene yield. This is thought to be due to the reaction of the increased amount of ethylene with excess benzene. The reduced benzene/ethylene mole ratio resulted in greater diethylbenzene production along with increased heavies production. However, this was offset by a decrease in toluene production. Based upon the experimental work, the desirable benzene/ethylene mole ratios are within the range of 5–30, 8–25 preferably, and, more preferably, about 10–14.

TABLE 8

| Benzene/C2 = Mole Ratio | 11.74 | 11.74 | 11.74 | 9.82 | 9.82 | 9.82 | 7.81 | 7.86 | 7.86 |
|---|---|---|---|---|---|---|---|---|---|
| Catage/Hour | 0.5 | 1.0 | 2.0 | 2.83 | 3.83 | 19.08 | 43.33 | 88.83 | 70.83 |
| EB, wt % | 9.63 | 9.76 | 9.69 | 11.57 | 11.41 | 11.22 | 12.83 | 12.13 | 12.07 |
| Yield rel to EB | | | | | | | | | |
| Toluene, PPM | 727 | 717 | 722 | 605 | 605 | 606 | 530 | 561 | 555 |
| Xylenes, PPM | 0 | 0 | 0 | 0 | 0 | 0 | 0 | 0 | 0 |
| Cumene, PPM | 0 | 0 | 0 | 0 | 0 | 0 | 0 | 0 | 0 |
| Ethyltoluene, PPM | 0 | 0 | 0 | 0 | 0 | 0 | 0 | 0 | 0 |
| Butylbenzene, PPM | 1008 | 737 | 660 | 761 | 753 | 686 | 841 | 841 | 837 |
| DEB. wt % | 5.72 | 5.81 | 5.79 | 7.01 | 7.05 | 7.21 | 9.32 | 9.35 | 9.36 |
| Heavies, wt % | 0.51 | 0.48 | 0.41 | 0.49 | 0.45 | 0.42 | 0.64 | 0.63 | 0.66 |
| % Mole Selectivity | | | | | | | | | |
| Xylenes | 0 | 0 | 0 | 0 | 0 | 0 | 0 | 0 | 0 |
| EB | 94.09 | 94.03 | 94.12 | 93.47 | 93.37 | 93.23 | 90.26 | 89.49 | 88.61 |
| DEB | 4.26 | 4.32 | 4.31 | 5.18 | 5.21 | 5.32 | 6.65 | 6.62 | 6.63 |
| EB + DEB | 98.35 | 98.35 | 98.44 | 98.65 | 98.58 | 98.54 | 96.92 | 96.11 | 95.24 |

The alkylation reaction of the present invention can be carried out in either the liquid phase or vapor phase, but as indicated previously, it is preferred in carrying out the present invention to operate the alkylation reactor in the liquid phase. In this embodiment of the invention the alkylation reaction is carried out at pressures well above the vapor pressure of the aromatic substrate at the reaction temperature involved in order to ensure that a liquid phase is retained throughout the reactor. In order to provide a complete liquid phase reaction, a flooded bed format is used in which the catalyst is completely immersed in liquid. This can readily be accomplished by using an upflow technique such as used in the foregoing experimental work, and this usually will be preferred in carrying out the invention. However, a downflow flooded bed operation can be accomplished by control of the outlet flow rate to ensure that the catalyst beds are covered by liquid benzene or other aromatic substrate.

Figure 6:
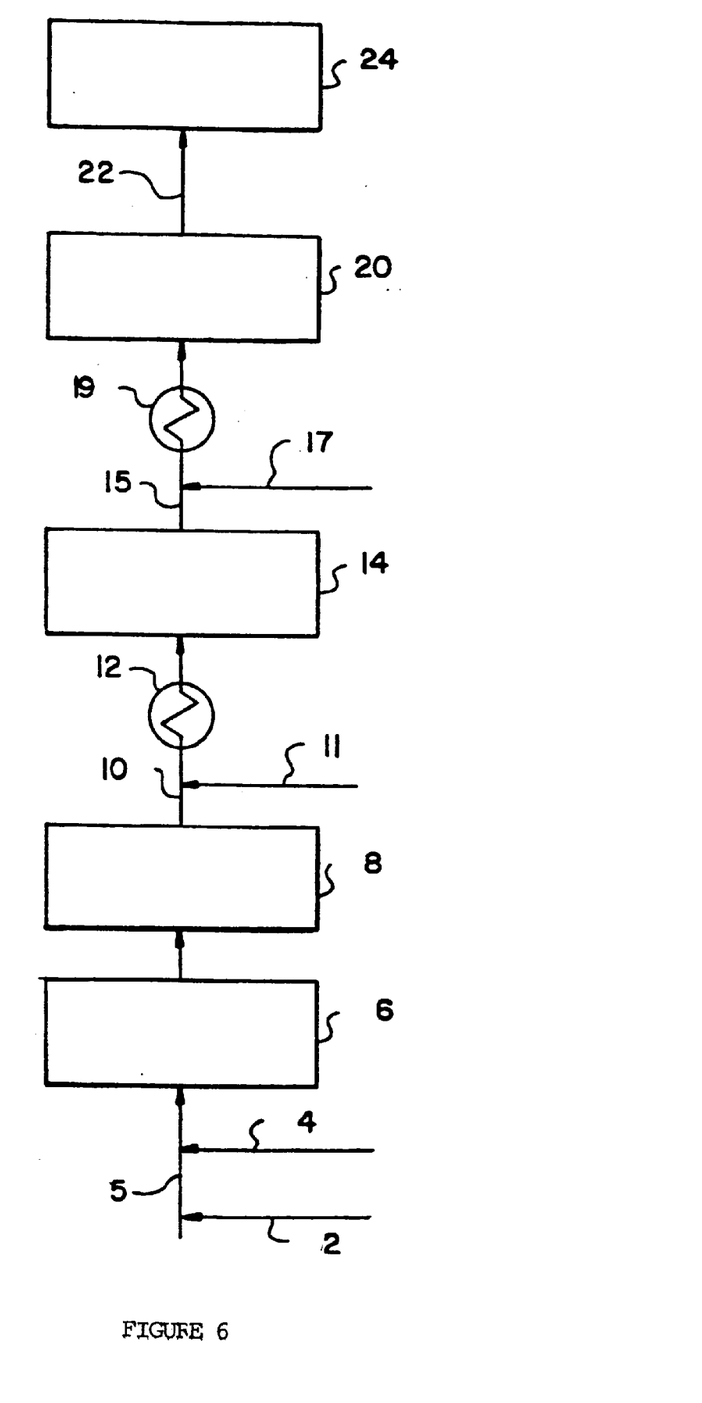
FIG. 6 is a schematic illustration of a staged reactor system which can be used in carrying out the present invention.

Preferably, a staged reaction format is employed in order to ensure good solubility of the ethylene (or other alkylating agent) in the benzene (or other aromatic substrate) and provide that the entire reaction takes place in the liquid phase. The staged reaction format may be provided by a plurality of catalyst beds in a single reactor by a series of sequentially-connected reactors as disclosed in U.S. Pat. No. 5,196,623 to Butler. The provision of multiple stages provides an opportunity for interstage cooling where adiabatic reactors are used or permits the use of several isothermal reaction stages. Turning now to FIG. 6, there is shown a schematic illustration of a staged reactor system used for the production of ethylbenzene by the reaction of ethylene with benzene which includes a plurality of adiabatic reactors with interstage cooling and injection of ethylene. More particularly and as illustrated in the drawing, ethylene and benzene are supplied via lines 2 and 4 to the inlet line 5 of a dehydration unit 6. The dehydration unit functions to dehydrate the input to the alkylation reactors so that it is essentially dry, desirably containing less than 100 ppm water and more preferably less than 50 ppm water. By way of example, dehydrator 6 may take the form of a packed column packed with a desiccant such as silica gel or other suitable hydroscopic medium.

The dehydrator effluent is supplied to a reactor 8, the first of a plurality of series connected alkylation reactors operated in an upflow mode. Reactor 8 is operated at an average temperature of 300° C. or less and preferably at an average temperature within the range of 150°–250° C. The pressure on a reactor 8 is sufficient to maintain the benzene in the liquid phase and preferably is at least 50 psi above the vapor pressure of the benzene at the reactor temperature. Typically, the reactor pressure is within the range of about 500–650 psia. The remaining downstream reactors normally are operated under approximately the same conditions as the initial reactor. The effluent from the initial reactor 8 is withdrawn via line 9 and applied through a heat exchanger 12 where it is cooled prior to being supplied to the second stage reactor 14. Ethylene is supplied via line 11 where it is mixed with the effluent from the first reactor 8. Preferably, the ethylene is supplied to the reactor effluent prior to cooling as shown in the drawing in order to facilitate distribution of the ethylene throughout the liquid benzene. Desirably, the cooling step is carried out to reduce the temperature of the feed mixture supplied to the second reactor 14 to a value about the same as the inlet temperature to the first reactor 8. The average temperature in the second reactor normally will be about the same as that of the first reactor. The pressure will of necessity be somewhat lower in order to provide for sufficient pressure gradient to accommodate flow through the system. The effluent from the second reactor 14 is supplied along with ethylene provided via line 17 to a second interstage cooling unit 19 where the charge mixture to third reactor 20 is again cooled to a temperature about equal to the inlet temperature for the first two reactors.

The output from reactor 20 is supplied via line 22 to a down-stream separation and processing unit 24. In unit 24, ethylbenzene is separated and withdrawn as the product of the alkylation plant. Typically, ethylbenzene will be used as the charge to a dehydrogenation system where it undergoes catalytic dehydrogenation in the production of styrene. Normally, benzene and ethylene will be separated in unit 24 and recycled for use in the alkylation process. Heavier polyethylbenzenes may be transalkylated with benzene to produce additional ethylbenzene. A suitable multistage separation system together with a transalkylation system may take the form of one of the integrated systems disclosed in the aforementioned EPA 467,007, the entire disclosure of which is incorporated herein by reference. Stoichiometric excess of benzene to ethylene will be supplied in the charge stock to the alkylation reactors in order to enhance selectivity for monoalkylation. Operation of the reactors to provide liquid phase alkylation under relatively mild conditions not only minimizes the xylene produced in the alkylation reaction but also enables the use of a somewhat lower benzene/ethylene molar ratio than is usually the case. Benzene/ethylene molar ratios as low as about 2:1 may be employed, although ratios of about 5:1 usually will be used. However, there is usually little incentive to use extremely high ratios, and as a practical matter, the benzene/ethylene molar ratio will seldom exceed 15:1. Preferred benzene/ethylene mole ratios are about 10–14. The benzene/ethylene mole ratios referred to above are with respect to the overall system, and for a multi-stage reaction system, such as depicted in the drawing, the benzene/ethylene ratio of the feed to each stage will be less than the overall ratio. The amount of ethylene solubilized in the benzene charge to each reactor stage will depend in part upon the number of reactor stages employed. Normally, at least three reactor stages, as illustrated, will be used. Additional reactor stages will be provided although the total number of stages normally will not exceed 8. Preferably, the pressure in each reaction stage and the amount of ethylene supplied therein is such as to provide at least 1 mole percent of ethylene solubilized in the benzene. Usually, at least 2 mole percent of ethylene will be solubilized in the charge to each reactor. Unless a great many reactor stages are employed, usually the amount of ethylene solubilized in the liquid benzene phase of each reactor will be at least 4 mole percent.

Multistage ethylation of benzene may also be carried out in accordance with the present invention employing isothermal reaction zones. Isothermal reactors can take the form of shell and tube type heat exchangers with the alkylation catalyst deposited within the tubes and with a heat transfer medium circulated through the shell surrounding the catalyst-filled tubes. The heat exchange medium will of course be supplied through the reactors at rates to maintain a relatively constant temperature across each reaction stage. In this case interstage cooling will be unnecessary although it will be preferred to inject ethylene at the front of each reaction stage.

Having described specific embodiments of the present invention, it will be understood that modifications thereof may be suggested to those skilled in the art, and it is intended to cover all such modifications as fall within the scope of the appended claims.

What is claimed:

1. In a method for the alkylation of an aromatic compound, the steps comprising:
   (a) supplying a feed stock containing an aromatic substrate into a reaction zone and into contact with a molecular sieve catalyst comprising a modified zeolite beta alkylation catalyst having an intergrowth of a ZSM-12 crystalline framework within the crystalline framework of zeolite beta;
   (b) supplying an alkylating agent to said reaction zone;
   (c) operating said reaction zone at temperature and pressure conditions effective to affect alkylation to said aromatic substrate by said alkylating agent; and
   (d) recovering alkylated aromatic substrate from said reaction zone.

2. The method of claim 1 wherein said molecular sieve catalyst is characterized by an x-ray diffraction pattern characteristic of zeolite beta and having a maximum peak at an interplanar spacing D of 4.0/±0.1A and secondary peaks $S_1$ at a D spacing of 11.4±0.2A, $S_2$ at a D spacing of 4.2±0.1A and a secondary doublet $S_3$, $S_4$ at D spacings within the range of about 3.0–3.4±0.1A, and further comprising a first secondary peak characteristic of ZSM-12 occurring at an interplanar spacing D 10.0±2A and additional secondary peaks characteristic of ZSM-12 at D spacings less than the D spacing of said primary peak but greater than the D spacing of said doublet $S_3$, $S_4$.

3. The method of claim 1 wherein said molecular sieve catalyst is in the hydrogen form.

4. The method of claim 1 wherein said molecular sieve catalyst incorporates lanthanum ions in the crystalline structure of said molecular sieve.

5. The method of claim 1 wherein said aromatic substrate is benzene and said alkylating agent is a $C_2$–$C_4$ alkylating agent.

6. The method of claim 5 wherein said alklating agent is an ethylating agent.

7. The method of claim 6 wherein said ethylating agent is ethylene.

8. The method of claim 6 wherein said aromatic substrate and said alkylating agent are supplied to provide a benzene/ethylation mole ratio within the range of 8–25.

9. The method of claim 6 wherein said reaction zone comprises a plurality of series-connected reaction stages containing said modified zeolite beta catalysts and supplying said aromatic feed stock to the first of said reaction stages with the effluent from said first reaction stage supplied to at least a second of said reaction stages along with separately supplying the ethylating agent to each of said first and second reaction stages.

10. In a method for the production of ethyl benzene by the liquid phase ethylation of benzene, the steps comprising:

(a) supplying a benzene containing feed stock into a reaction zone containing a molecular sieve alkylation catalyst comprising a modified zeolite beta alkylation catalyst having an intergrowth of a ZSM-12 crystalline framework with the crystalline framework of zeolite beta;

(b) supplying an ethylating agent to said reaction zone;

(c) operating said reaction zones at temperature and pressure conditions to maintain said benzene in the liquid phase to cause monoethylation of said benzene in the liquid phase in the presence of said catalyst and under conditions in which xylene produced in said reaction zone is no more than 0.05 wt. % based upon the amount of ethyl benzene produced; and (d) recovering ethyl benzene from said reaction zone.

11. The process of claim 10 wherein the amount of toluene produced in said reaction zone is no more than 0.1 wt. % based upon the amount of ethyl benzene produced.

12. The method of claim 10 wherein said molecular sieve catalyst is in the hydrogen form.

13. The method of claim 10 wherein said molecular sieve catalyst incorporates lanthanum ions in the crystalline structure of said molecular sieve.

14. The method of claim 10 wherein said ethylating agent is ethylene.

15. The method of claim 14 wherein said benzene containing feedstock and said ethylene are supplied to said reaction zone to provide a benzene/ethylene mole ratio within the range of 10–14.

16. The method of claim 10 wherein said reaction zone comprises a plurality of series-connected reaction stages containing said modified zeolite beta catalyst and supplying said aromatic feed stock to the first of said reaction stages with the effluent from said first reaction stage supplied to at least a second of said reaction stages along with separately supplying the ethylating agent to each of said first and second reaction stages.

17. In a method for the production of ethyl benzene by the liquid phase ethylation of benzene, the steps comprising:

(a) supplying a benzene containing feed stock into a reaction zone containing a molecular sieve alkylation catalyst characterized by an x-ray diffraction pattern characteristic of zeolite beta and having a maximum peak at an interplanar spacing D of 4.0/±0.1A and secondary peaks $S_1$ at a D spacing of 11.4±0.2A, $S_2$ at a D spacing of 4.2±0.1A and a secondary doublet $S_3$, $S_4$ at D spacings within the range of about 3.0–3.4±0.1A, and further comprising a first secondary peak characteristic of ZSM-12 occurring at an interplanar spacing D 10.0±2A and additional secondary peaks characteristic of ZSM-12 at D spacings less than the D spacing of said primary peak but greater than the D spacing of said doublet $S_3$, $S_4$;

(b) supplying an ethylene agent to said reaction zone;

(c) operating said reaction zones at temperature and pressure conditions to maintain said benzene in the liquid phase to cause monoethylation of said benzene in the liquid phase in the presence of said catalyst; and (d) recovering ethyl benzene from said reaction zone.

18. The method of claim 17 wherein said reaction zone is operated under conditions in which the amount of xylene produced in said reaction zone is no more than 0.05 wt. % based upon the amount of ethyl benzene produced.

19. The process of claim 17 wherein the amount of toluene produced in said reaction zone is no more than 0.1 wt. % based upon the amount of ethyl benzene produced.

20. The method of claim 17 wherein said reaction zone comprises a plurality of series-connected reaction stages containing said molecular sieve alkylation catalyst and supplying said aromatic feed stock to the first of said reaction stages with the effluent from said first reaction stage supplied to at least a second of said reaction stages along with separately supplying the ethylating agent to each of said first and second reaction stages.

21. The method of claim 20 wherein said molecular sieve alkylation catalyst is in the hydrogen form.

22. The method of claim 21 wherein said molecular sieve catalyst incorporates lanthanum ions in the crystalline structure of said molecular sieve.

* * * * *

UNITED STATES PATENT AND TRADEMARK OFFICE
CERTIFICATE OF CORRECTION

PATENT NO.    : 5,907,073
DATED         : May 25, 1999
INVENTOR(S)   : Ashim Kumar Ghosh It is certified that error appears in the above-identified patent and that said Letters Patent is hereby corrected as shown below:

<u>Drawings,</u>
Fig. 2, should read as follows:

UNITED STATES PATENT AND TRADEMARK OFFICE
CERTIFICATE OF CORRECTION

PATENT NO.    : 5,907,073
DATED         : May 25, 1999
INVENTOR(S)   : Ashim Kumar Ghosh It is certified that error appears in the above-identified patent and that said Letters Patent is hereby corrected as shown below:

<u>Drawings (cont'd),</u>
Figs. 4 & 5, should read as follows:

FIG.4

FIG.5

Signed and Sealed this

Seventh Day of October, 2003

JAMES E. ROGAN
*Director of the United States Patent and Trademark Office*